United States Patent
Park et al.

(10) Patent No.: US 11,602,464 B2
(45) Date of Patent: Mar. 14, 2023

(54) MULTI-LAYER MATERIAL FOR USE IN AN ABSORBENT ARTICLE

(71) Applicant: Kimberly-Clark Worldwide, Inc., Neenah, WI (US)

(72) Inventors: HyungWoo Park, Suwon-si (KR); SungYeon Hong, Liege (BE); SeongDae Roh, Appleton, WI (US); JuHyung Lee, Anyang-si (KR); Moonyoung Cho, Yongin-si (KR); HyoungKun Park, Yongln-si (KR); YeonJung Kim, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 1100 days.

(21) Appl. No.: 16/095,403

(22) PCT Filed: Apr. 29, 2016

(86) PCT No.: PCT/US2016/030062
§ 371 (c)(1),
(2) Date: Oct. 22, 2018

(87) PCT Pub. No.: WO2017/188983
PCT Pub. Date: Nov. 2, 2017

(65) Prior Publication Data
US 2019/0133833 A1    May 9, 2019

(51) Int. Cl.
*A61F 13/15* (2006.01)
*A61F 13/535* (2006.01)
(Continued)

(52) U.S. Cl.
CPC ...... *A61F 13/15203* (2013.01); *A61F 13/472* (2013.01); *A61F 13/51108* (2013.01);
(Continued)

(58) Field of Classification Search
CPC .......... A61F 13/15203; A61F 13/51104; A61F 13/51108; A61F 13/5116; A61F 13/535;
(Continued)

(56) References Cited

U.S. PATENT DOCUMENTS 2,982,667 A    5/1961  Lints et al.
3,808,094 A    4/1974  McKnight et al.
(Continued)

FOREIGN PATENT DOCUMENTS

CN    105120817 A    12/2015
EP      2901992 A1     8/2015
(Continued)

OTHER PUBLICATIONS

Malkan, Overview of Nonwovens From Fiber Producers Perspective, 1999, The University of Tennessee, vol. 2:1346-1353.*

*Primary Examiner* — Michele M Kidwell
(74) *Attorney, Agent, or Firm* — Kimberly-Clark Worldwide, Inc.

(57) ABSTRACT

An absorbent article which can have an improved vertical absorption capability in the depth direction of the absorbent article. The absorbent article can have a topsheet layer, a backsheet layer, and an absorbent system positioned between the topsheet layer and the backsheet layer. The absorbent system can have at least a fluid intake layer and an absorbent core. The fluid intake layer can provide the absorbent article with a raised portion which can improve the vertical absorption capability in the depth direction of the absorbent article.

15 Claims, 6 Drawing Sheets

(51) Int. Cl.
  *A61F 13/537* (2006.01)
  *A61F 13/511* (2006.01)
  *A61F 13/536* (2006.01)
  *A61F 13/538* (2006.01)
  *A61F 13/472* (2006.01)

(52) U.S. Cl.
  CPC .......... *A61F 13/535* (2013.01); *A61F 13/536* (2013.01); *A61F 13/538* (2013.01); *A61F 13/53713* (2013.01); *A61F 13/53747* (2013.01); *A61F 13/5116* (2013.01); *A61F 13/51104* (2013.01); *A61F 2013/15357* (2013.01); *A61F 2013/15373* (2013.01); *A61F 2013/15943* (2013.01)

(58) Field of Classification Search
  CPC .............. A61F 13/536; A61F 13/53713; A61F 13/53747; A61F 13/538; A61F 2013/15357; A61F 2013/15373; A61F 2013/15943
  See application file for complete search history.

(56) References Cited

U.S. PATENT DOCUMENTS

| | | |
|---|---|---|
| 5,809,805 A | 9/1998 | Palmer et al. |
| 6,168,584 B1 | 1/2001 | Allen et al. |
| 7,037,298 B2 | 5/2006 | Ohshima et al. |
| 8,466,334 B2 | 6/2013 | Takeuchi et al. |
| 2001/0044610 A1* | 11/2001 | Kim .................. A61F 13/53747 604/365 |
| 2002/0169430 A1 | 11/2002 | Kirk et al. |
| 2004/0016091 A1 | 1/2004 | Rivera et al. |
| 2004/0176733 A1 | 9/2004 | Glaug et al. |
| 2006/0068673 A1* | 3/2006 | Goene .................... D04H 1/435 442/409 |
| 2012/0238978 A1 | 9/2012 | Weisman et al. |
| 2012/0238982 A1* | 9/2012 | Weisman .......... A61F 13/53747 604/370 |
| 2012/0277711 A1 | 11/2012 | Kim et al. |
| 2013/0143020 A1 | 6/2013 | Wood et al. |
| 2013/0143462 A1 | 6/2013 | Wood et al. |
| 2013/0165885 A1 | 6/2013 | Kurihara |
| 2013/0198998 A1 | 8/2013 | Kuhn et al. |
| 2015/0005729 A1 | 1/2015 | Nakao et al. |
| 2016/0067118 A1* | 3/2016 | Hammons ............... B32B 5/022 428/137 |

FOREIGN PATENT DOCUMENTS

| | | | |
|---|---|---|---|
| WO | WO9612460 A1 | 5/1996 | |
| WO | 2014/085974 | * 6/2014 | ............ A61F 13/511 |

* cited by examiner

MULTI-LAYER MATERIAL FOR USE IN AN ABSORBENT ARTICLE

BACKGROUND OF THE DISCLOSURE

Products such as absorbent articles are often used to collect and retain human body exudates containing, for example, urine, menses and/or blood. Comfort, absorbency, and discretion are three main product attributes and areas of concern for the wearer of the product. In particular, a wearer is often interested in knowing that such products will absorb significant volumes of body exudates with minimal leakage in order to protect their undergarments, outer garments, or bedsheets from staining, and that such products will help them avoid the subsequent embarrassment brought on by such staining.

Currently, a wide variety of products for absorption of body exudates are available in the form of feminine pads, sanitary napkins, panty shields, pantiliners, and incontinence devices. These products generally have an absorbent core positioned between a body-facing liquid permeable topsheet layer and a garment-facing liquid impermeable backsheet layer. The edges of the topsheet and the backsheet layers are often bonded together at their periphery to form a seal to contain the absorbent core and body exudates received into the product through the topsheet layer. In use, such products are typically positioned in the crotch portion of an undergarment for absorption of the body exudates and a garment attachment adhesive on the backsheet layer can be used to attach the product to the inner crotch portion of the undergarment. Some of these products can also include wing-like structures for wrapping about the wearer's undergarment to further secure the product to the undergarment and to protect the undergarment from staining. Such wing-like structures (also known as flaps or tabs) are frequently made from lateral extensions of the topsheet and/or backsheet layers.

In a conventional absorbent article, the absorbent core is generally flat and thin in an effort to provide more comfort to the wearer of the absorbent article. This design of the absorbent article can ultimately lead to early failure of the absorbent article as the body exudates can follow the contour of the body of the wearer prior to being absorbed into the absorbent article. If the body exudates cannot be efficiently absorbed into the absorbent article, they may run off the edge of the absorbent article causing leakage and staining.

As a result, there remains a need for an improved product, such as an absorbent article, that has an improved vertical absorption capability.

SUMMARY OF THE DISCLOSURE

In various embodiments, a material for use in an absorbent article comprises a first material layer and a second material layer bonded together, wherein the first material layer comprises from 2 to 16 sublayers. In various embodiments, the first material layer is a lapped through air bonded carded web. In various embodiments, the first material layer is a cross lapped through air bonded carded web. In various embodiments, a first of the sublayers has a first fiber orientation and a second of the sublayers has a second fiber orientation wherein the first fiber orientation and the second fiber orientation are different from about 15 to about 120 degrees. In various embodiments, the second material layer is an airlaid material.

In various embodiments, the material has a thickness from about 2 mm to about 15 mm. In various embodiments, the material has a Compression Work from about 3 gf cm/cm$^2$ to about 10 gf cm/cm$^2$. In various embodiments, the material has a Compression Rate from about 40% to about 100%.

In various embodiments, an absorbent article comprises a longitudinal direction, a transverse direction, and a depth direction; a topsheet layer and a backsheet layer; and an absorbent system positioned between the topsheet layer and the backsheet layer, the absorbent system comprising a fluid intake layer comprising a material comprising a first material layer and a second material layer bonded together, wherein the first material layer comprises from 2 to 16 sublayers; and an absorbent core. In various embodiments, the first material layer is a lapped through air bonded carded web. In various embodiments, the first material layer is a cross lapped through air bonded carded web. In various embodiments, a first of the sublayers has a first fiber orientation and a second of the sublayers has a second fiber orientation wherein the first fiber orientation and the second fiber orientation are different from about 15 to about 120 degrees. In various embodiments, the second material layer is an airlaid material.

In various embodiments, the fluid intake layer defines a raised portion. In various embodiments, the absorbent article has a first height at the location of the raised portion from about 3.5 mm to about 10 mm. In various embodiments, the absorbent article has a Compression Work from about 4 to about 8 gf cm/cm$^2$. In various embodiments, the absorbent article has a Compression Rate from about 30 to about 75%. In various embodiments, the fluid intake layer further comprises an opening.

In various embodiments, the absorbent article further comprises an embossed region. In various embodiments, the embossed region does not penetrate into the fluid intake layer. In various embodiments, the embossed region is separated from the fluid intake layer a distance from about 1 mm to about 5.5 mm. In various embodiments, the absorbent article further comprises a second embossed region.

In various embodiments, the fluid intake layer has a body facing surface area and the absorbent article has a total body facing surface area wherein the body facing surface area of the fluid intake layer is from about 5% to about 20% of the total body facing surface area of the absorbent article.

Repeat use of reference characters in the present specification and drawings is intended to represent the same or analogous features or elements of the disclosure.

DETAILED DESCRIPTION OF THE DISCLOSURE

The present disclosure is generally directed towards an absorbent article which can have an improved vertical absorption capability in the depth direction of the absorbent article. An absorbent article can have a longitudinal direction, a transverse direction, and a depth direction. The absorbent article can have a topsheet layer, a backsheet layer, and an absorbent system positioned between the topsheet layer and the backsheet layer. The absorbent system can have at least a fluid intake layer and an absorbent core. The fluid intake layer can be positioned between the topsheet layer and the absorbent core in the depth direction of the absorbent article. The fluid intake layer can provide the absorbent article with a raised portion which can improve the vertical absorption capability in the depth direction of the absorbent article.

Definitions:

As used herein, the term "absorbent article" refers herein to a garment or other end-use personal care absorbent article, including, but not limited to, catamenial products, such as sanitary napkins, feminine pads, pantiliners, and panty shields, incontinence devices, and the like.

As used herein, the term "airlaid" refers herein to a web manufactured by an airlaying process. In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers herein to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, chemical bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form one fiber. Conjugate fibers are also sometimes referred to as bicomponent fibers or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al. each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10 or 20 gsm to about 120, 125 or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent" or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in part on ionicity (a factor of the ionic concentration of the aqueous solution), and the SAP functional polar groups that have an affinity for water. SAP are typically made from the polymerization of acrylic acid blended with sodium hydroxide in the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating on another material or fiber.

The term "thermoplastic" refers herein to a material which softens and which can be shaped when exposed to heat and which substantially returns to a non-softened condition when cooled.

The term "wearer" refers herein to one who uses an absorbent article, such as, but not limited to, a diaper, training pant, youth pant, incontinent product, feminine napkin, or other absorbent article and the absorbent article is placed in proximity to the body to capture body exudates.

Absorbent Article:

The present disclosure is generally directed towards an absorbent article which can have an improved vertical absorption capability in the depth direction of the absorbent article. An absorbent article can have a longitudinal direction, a transverse direction, and a depth direction. The absorbent article can have a topsheet layer, a backsheet layer, and an absorbent system positioned between the topsheet layer and the backsheet layer. The absorbent system can have at least a fluid intake layer and an absorbent core. The fluid intake layer can be positioned between the topsheet layer and the absorbent core in the depth direction of the absorbent article. The fluid intake layer can provide the absorbent article with a raised portion which can improve the vertical absorption capability in the depth direction of the absorbent article.

Figure 1:
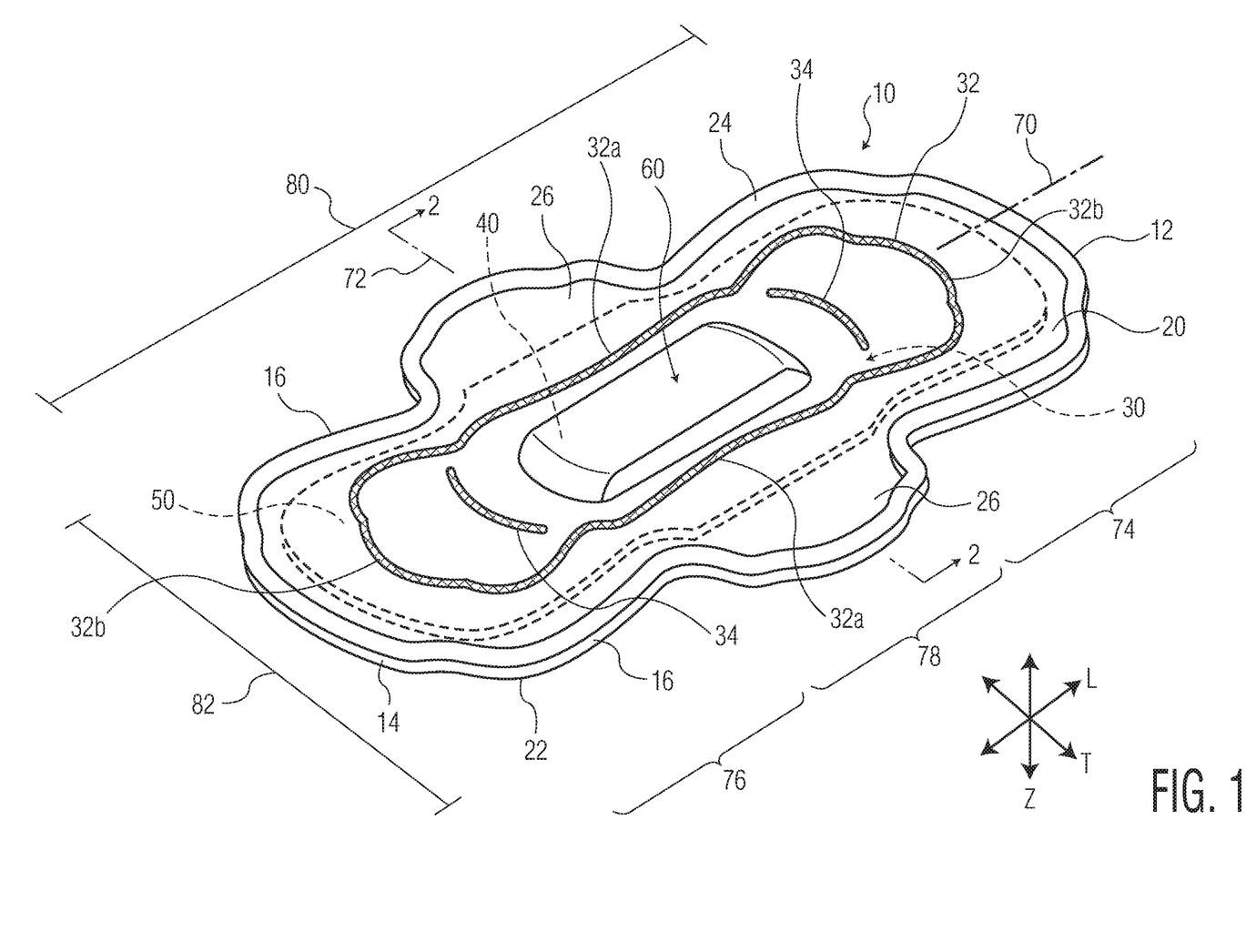
FIG. 1 is a perspective view of an embodiment of an absorbent article.
Figure 2:
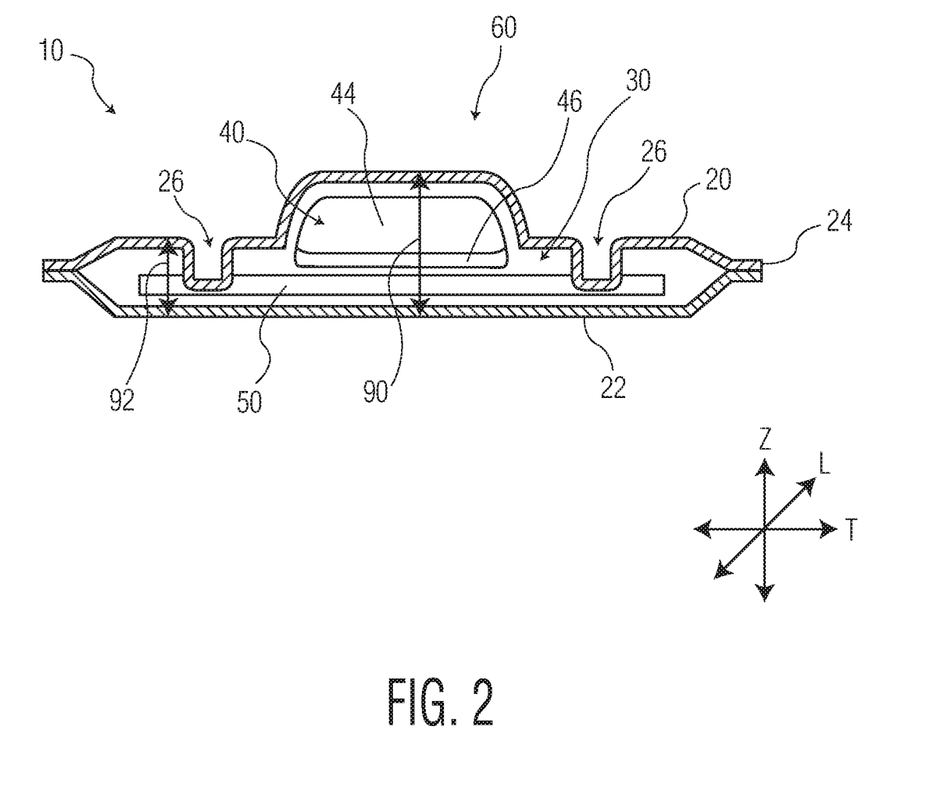
FIG. 2 is a cross-sectional view of the absorbent article of FIG. 1 taken along line 2-2.
Figure 3:
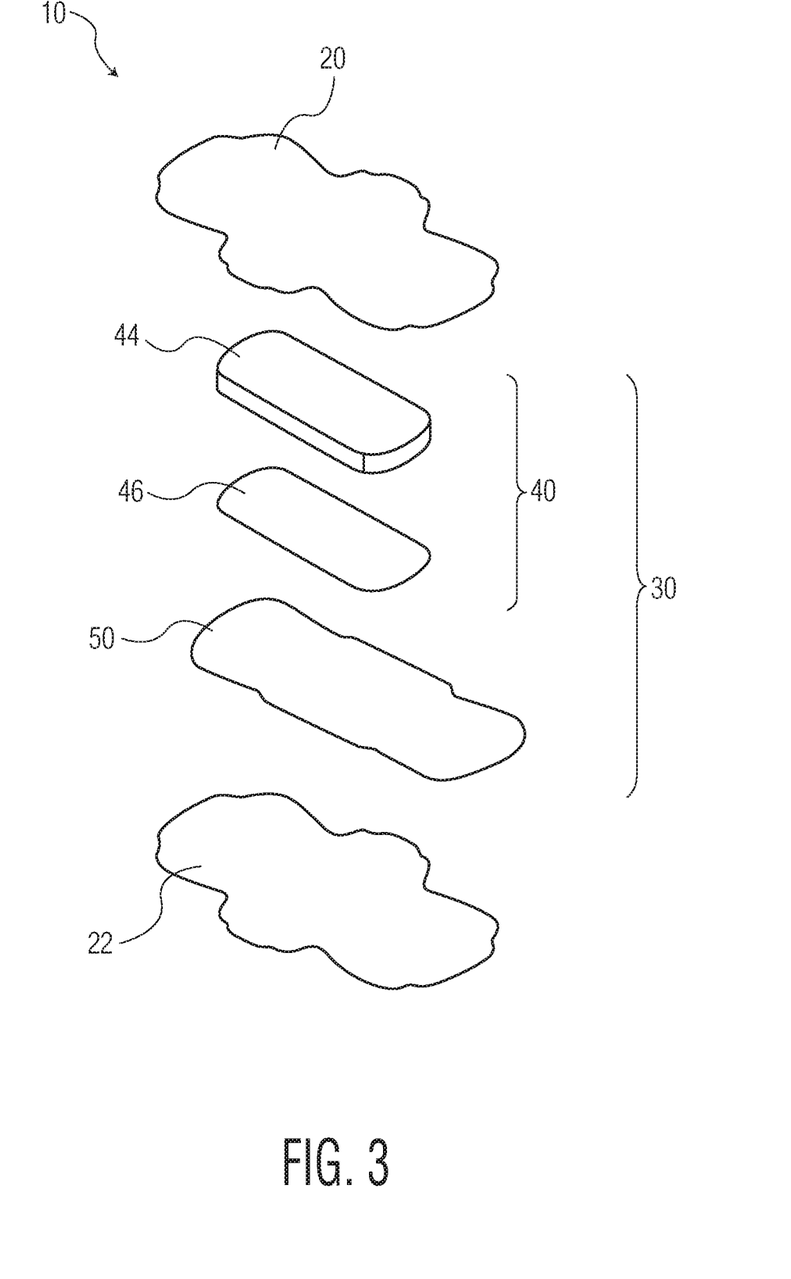
FIG. 3 is an exploded perspective view of the absorbent article of FIG. 1.

Referring to FIGS. 1-3, FIG. 1 provides an illustration of a perspective view of an exemplary absorbent article 10 in the form of a sanitary napkin with wings, FIG. 2 provides an illustration of a cross-sectional view of the absorbent article 10 of FIG. 1 taken along line 2-2, and FIG. 3 provides an illustration of an exploded perspective view of the absorbent article 10 of FIG. 1.

The absorbent article 10 can have a longitudinal direction (L), a transverse direction (T), and a depth direction (Z). The absorbent article 10 can have a first transverse direction end edge 12, a second transverse direction end edge 14 opposite the first transverse direction end edge 12, and a pair of opposing longitudinal direction side edges 16. The absorbent article 10 can have a wearer facing, liquid permeable topsheet layer 20 and a garment facing, liquid impermeable backsheet layer 22. An absorbent system 30 can be positioned between the topsheet layer 20 and the backsheet layer 22. The absorbent system 30 can include a fluid intake layer 40 and an absorbent core 50. The fluid intake layer 40 can provide the absorbent article 10 with a raised portion 60. A portion of the absorbent article 10 can define a first absorbent article height 90 in the depth direction (Z) of the absorbent article 10 and a different portion of the absorbent article 10 can define a second absorbent article height 92 in the depth direction (Z) of the absorbent article 10. In various embodiments, the absorbent article 10 can take on various geometries but will generally have a pair of opposing longitudinal direction side edges 16 and a pair of opposing transverse direction end edges, 12 and 14.

The topsheet layer 20 and the backsheet layer 22 can both extend beyond the outermost peripheral edges of the absorbent system 30 and can be peripherally bonded together, either entirely or partially, using known bonding techniques to form a sealed peripheral region 24. For example, the topsheet layer 20 and the backsheet layer 22 can be bonded together by adhesive bonding, ultrasonic bonding, or any other suitable bonding method known in the art.

In various embodiments, such as illustrated in FIG. 1, the absorbent article 10 can have a pair of wings 26 extending outwardly, in the transverse direction (T), from the absorbent article 10. The wings 26 can drape over the edges of the wearer's undergarment so that the wings 26 are disposed between the edges of the wearer's undergarment and her thighs. The wings 26 can serve at least two purposes. First, the wings 26 can prevent soiling of the wearer's undergarment by forming a barrier along the edges of the undergarment. Second, the wings 26 can be provided with an attachment aid, such as, for example, a garment attachment adhesive or a hook, to keep the absorbent article 10 securely and properly positioned in the undergarment. The wings 26 can wrap around the crotch region of the wearer's undergarment to aid in securing the absorbent article 10 to the wearer's undergarment when in use. Each wing 26 can fold under the crotch region of the wearer's undergarment and the attachment aid can either form a secure attachment to the opposite wing 26 or directly to the surface of the wearer's undergarment. In various embodiments, the wings 26 can be an extension of materials forming the topsheet layer 20, the backsheet layer 22, and/or the absorbent system 30 such that the wings 26 can be of a unitary construction with the absorbent article 10. In various embodiments, the wings 26 can be constructed of materials similar to the topsheet layer 20, the backsheet layer 22, the absorbent system 30, or combinations of these materials. In various embodiments, the wings 26 can be separate elements bonded to the main body of the absorbent article 10. It is to be understood that the wings 26 are optional and, in various embodiments, an absorbent article 10 can be configured without wings 26.

The absorbent article 10 defines a longitudinal direction (L), a transverse direction (T), a depth direction (Z), a longitudinal centerline 70, and a transverse centerline 72. The absorbent article 10 includes a front portion 74, a rear portion 76, and a central portion 78 extending between the front portion 74 and the rear portion 76. In general, the front portion 74 of the absorbent article 10 is adapted to be worn towards the front of the wearer, the central portion 78 is adapted to be worn proximate the wearer's crotch, and the rear portion 76 is adapted to be worn towards the rear of the wearer. The absorbent article 10 also defines an absorbent article length 80 in the longitudinal direction (L) and an absorbent article width 82 in the transverse direction (T). The front portion 74 of the absorbent article 10 is defined as the front third of the absorbent article length 80, the central portion 78 is defined as the center third of the absorbent article length 80, and the rear portion 76 is defined as the rear third of the absorbent article length 80. In various embodiments, the absorbent article 10 can have an absorbent article length 80, as measured at the longitudinal centerline 70, from about 200, 210, or 220 mm to about 240, 280, or 320 mm. In various embodiments, the absorbent article 10 can have an absorbent article width 82, as measured at the transverse centerline 72, from about 130, 135, or 140 mm to about 150, 155, or 160 mm for absorbent articles 10 with wings 26. In various embodiments, the absorbent article 10 can have an absorbent article width 82, as measured at the transverse centerline 72, from about 50, 60, or 65 mm to about 75, 80 or 90 mm for absorbent articles 10 without wings 26.

Each of these components of the absorbent article 10, as well as additional components, will be described in more detail herein.

Topsheet Layer:

The topsheet layer 20 defines a wearer facing surface of the absorbent article 10 that may directly contact the body of the wearer and is liquid permeable to receive body exudates. The topsheet layer 20 is desirably provided for comfort and conformability and functions to direct body exudates away from the body of the wearer, through its own structure, and towards the absorbent system 30. The topsheet layer 20 desirably retains little to no liquid in its structure, so that it provides a relatively comfortable and non-irritating surface next to the skin of the wearer of the absorbent article 10.

The topsheet layer 20 can be a single layer of material, or alternatively, can be multiple layers that have been laminated together. The topsheet layer 20 can be constructed of any material such as one or more woven sheets, one or more fibrous nonwoven sheets, one or more film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a topsheet layer 20.

In various embodiments, the topsheet layer 20 can be constructed from various nonwoven webs such as meltblown webs, spunbond webs, hydroentangled spunlace webs, or through air bonded carded webs. Examples of suitable topsheet layer 20 materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable topsheet layer 20 can be a bonded carded web made of polypropylene and polyethylene such as that obtainable from Sandler Corporation, Germany. U.S. Pat. No. 4,801,494 to Datta, et al., and U.S. Pat. No. 4,908,026 to Sukiennik, et al., and WO 2009/062998 to Texol teach various other topsheet materials that may be used as the topsheet layer 20, each of which is hereby incorporated by reference thereto in its entirety. Additional topsheet layer 20 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

In various embodiments, the topsheet layer 20 may contain a plurality of apertures formed therethrough to permit body exudates to pass more readily into the absorbent system 30. The apertures may be randomly or uniformly arranged throughout the topsheet layer 20. The size, shape, diameter, and number of apertures may be varied to suit an absorbent article's 10 particular needs.

In various embodiments, the topsheet layer 20 can have a basis weight ranging from about 5, 10, 15, 20 or 25 gsm to about 50, 100, 120, 125 or 150 gsm. For example, in an embodiment, a topsheet layer 20 can be constructed from a through air bonded carded web having a basis weight ranging from about 15 gsm to about 100 gsm. In another example, a topsheet layer 20 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics and others.

In various embodiments, the topsheet layer 20 can be at least partially hydrophilic. In various embodiments, the hydrophilicity of the topsheet layer 20 can be increased or created via treatment of the topsheet layer 20 with surfactants. In various embodiments, a portion of the topsheet layer 20 can be hydrophilic and a portion of the topsheet layer 20 can be hydrophobic. In various embodiments, the portions of the topsheet layer 20 which can be hydrophobic can be either an inherently hydrophobic material or can be a material treated with a hydrophobic coating.

In various embodiments, the topsheet layer 20 can be a multicomponent topsheet layer 20 such as by having two or more different nonwoven or film materials, with the different materials placed in separate locations in the transverse direction (T) of the absorbent article 10. For example, referring to FIG. 6, the topsheet layer 20 can be a two layer or multicomponent material having a central portion 84 positioned along and straddling a longitudinal centerline 70 of the absorbent article 10, with lateral side portions 86 flanking and bonded to each side edge of the central portion 84. The central portion 84 can be constructed from a first material and the side portions 86 can be constructed from a material which can be the same as or different from the material of the central portion 84. In such embodiments, the central portion 84 may be at least partially hydrophilic and the side portions 86 may be inherently hydrophobic or may be treated with a hydrophobic coating. Examples of constructions of multi-component topsheet layers 20 are generally described in U.S. Pat. No. 5,961,505 to Coe, U.S. Pat. No. 5,415,640 to Kirby, and U.S. Pat. No. 6,117,523 to Sugahara, each of which is incorporated herein by reference thereto in its entirety.

Figure 6:
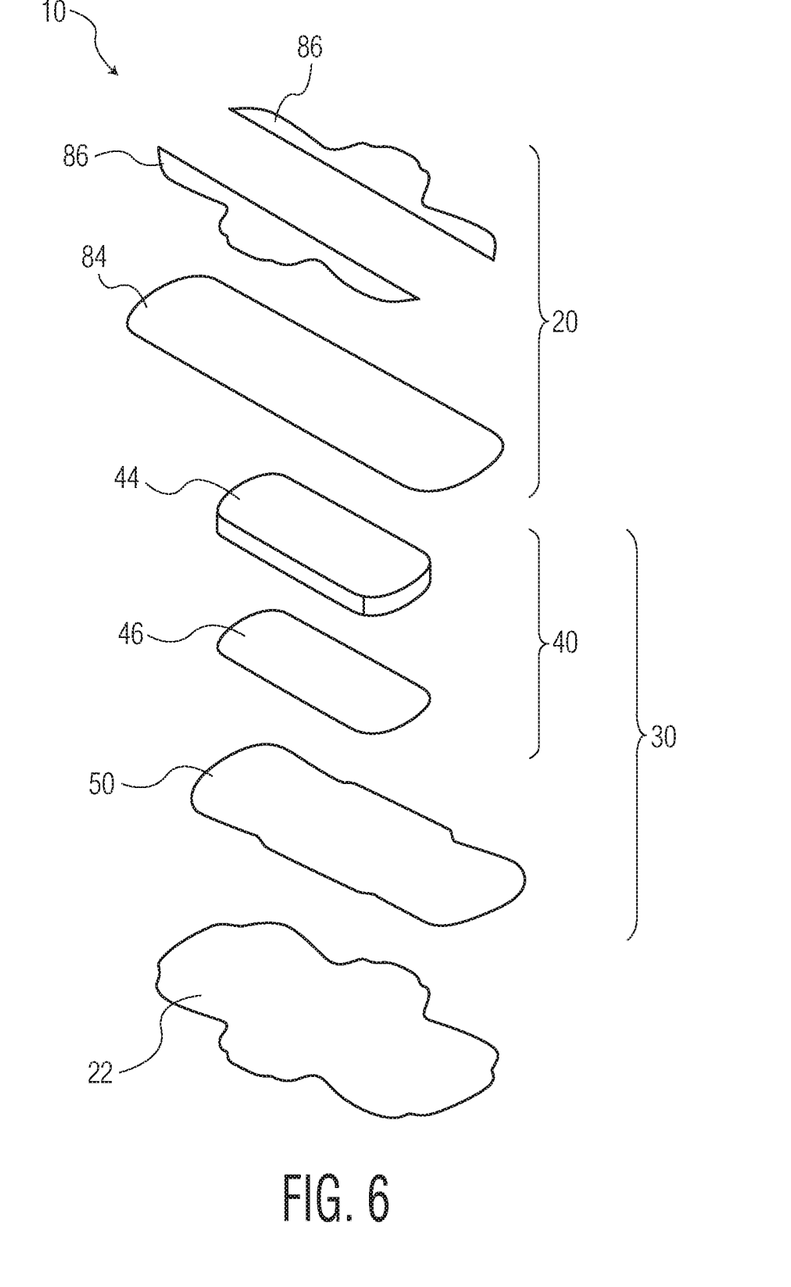
FIG. 6 is an exploded perspective view of an embodiment of an absorbent article.

In various embodiments, a central portion 84 of a topsheet layer 20 can be positioned symmetrically about the absorbent article 10 longitudinal centerline 70. Such central longitudinally directed central portion 84 can be a through air bonded carded web ("TABCW") having a basis weight between about 15 and about 100 gsm. Previously described nonwoven, woven, and apertured film topsheet layer materials may also be used as the central portion 84 of a topsheet layer 20. In various embodiments, the central portion 84 can be constructed from a TABCW material having a basis weight from about 20 to about 50 gsm such as is available from Xiamen Yanjan Industry, Beijing, DaYuan Nonwoven Fabrics, and others. Alternatively, apertured films, such as those available from such film suppliers as Texol, Italy and Tredegar, U.S.A. may be utilized. Different nonwoven, woven, or film sheet materials may be utilized as the side portions 86 of the topsheet layer 20. The selection of such topsheet layer 20 materials can vary based upon the overall desired attributes of the topsheet layer 20. For example, it may be desired to have a hydrophilic material in the central portion 84 and hydrophobic-barrier type materials in the side portions 86 to prevent leakage and increase a sense of dryness in the area of the side portions 86. Such side portions 86 can be adhesively, thermally, ultrasonically, or otherwise bonded to the central portion 84 along or adjacent the longitudinally directed side edges of the central portion 84. Traditional absorbent article construction adhesive may be used to bond the side portions 86 to the central portion 84. Either of the central portion 84 and/or the side portions 86 may be treated with surfactants and/or skin-health benefit agents, as are well known in the art.

Such longitudinally directed side portions 86 can be of a single or multi-layered construction. In various embodiments, the side portions 86 can be adhesively or otherwise bonded laminates. In various embodiments, the side portions 86 can be constructed of an upper fibrous nonwoven layer, such as a spunbond material, laminated to a bottom layer of a hydrophobic barrier film material. Such a spunbond layer may be formed from a polyolefin, such as a polypropylene and can include a wetting agent if desired. In various embodiments, a spunbond layer can have a basis weight from about 10 or 12 gsm to about 30 or 70 gsm and can be treated with hydrophilic wetting agents. In various embodiments, a film layer may have apertures to allow fluid to permeate to lower layers, and may be either of a single layer or multi-layer construction. In various embodiments, such film can be a polyolefin, such as a polyethylene having a basis weight from about 10 to about 40 gsm. Construction adhesive can be utilized to laminate the spunbond layer to the film layer at an add-on level of between about 0.1 gsm and 15 gsm. When a film barrier layer is used in the overall topsheet layer 20 design, it may include opacifying agents, such as film pigments, that can help the film in masking stains along the absorbent article 10 side edges, thereby serving as a masking element. In such a fashion, the film layer can serve to limit visualization of a fluid insult stain along the absorbent article 10 side edges when viewed from above the topsheet layer 20. The film layer may also serve as a barrier layer to prevent rewet of the topsheet layer 20 as well as to prevent the flow of fluid off the side edges of the absorbent article 10. In various embodiments, the side portions 86 can be laminates such as a spunbond-meltblown-meltblown-spunbond layer ("SMMS") laminate, spunbond-film laminate, or alternatively, other nonwoven laminate combinations.

Absorbent System:

The absorbent system 30 can include a fluid intake layer 40 and an absorbent core 50. The fluid intake layer 40 can provide the absorbent article 10 with a raised portion 60 which can improve the vertical absorption capability in the depth direction (Z) of the absorbent article. The raised portion 60 can allow body exudates to pass through the topsheet layer 20 and directly to the fluid intake layer 40 where the body exudates can be quickly absorbed by the fluid intake layer 40. Thus, it can be possible to minimize or prevent body exudates from leaking or oozing outwardly from the absorbent article 10 prior to the body exudates being ultimately absorbed into the absorbent system 30. It is to be understood that the absorbent system 30 may include additional layers in addition to the fluid intake layer 40 and the absorbent core 50.

Fluid Intake Layer:

The absorbent article 10 can include material such as a liquid permeable and resilient fluid intake layer 40 positioned between the topsheet layer 20 and the absorbent core 50. Such a fluid intake layer 40 can be made of a material that can be capable of rapidly transferring, in the depth direction (Z), body exudates that are delivered to the topsheet layer 20. The fluid intake layer 40 can generally have any shape and/or size desired. In an embodiment, the fluid intake layer 40 can have a curved rectangular shape, with a length equal to or less than the overall length of the absorbent article 10, and a width equal to or less than the width of the absorbent article 10. For example, the fluid intake layer 40 can have a longitudinal length from about 20, 40, or 60 mm to about 100, 150, 175, 200, or 300 mm and a transverse width from about 10, 15 or 20 mm to about 60, 80 or 100 mm may be utilized. The fluid intake layer 40 can have a basis weight from about 10, 25, or 100 gsm to about 150, 200, 250, or 300 gsm. The body facing surface of the absorbent article 10 can have a total surface area. The body facing surface of the fluid intake layer 40 can have a surface area which is smaller than the total surface area of the absorbent article 10. In comparison to the total surface area of the absorbent article 10, the body facing surface of the fluid intake layer 40 can have a surface area from about 5 or 10% to about 15 or 20%.

The resilient fluid intake layer 40 can be constructed as a multi-layer component of the absorbent article 10 formed from multiple layers of nonwoven material which are bonded together. For example, such as illustrated in FIGS. 2 and 3, the fluid intake layer 40 can have two material layers such as a first material layer 44 and a second material layer 46. The first material layer 44 can be positioned between the topsheet layer 20 and the second material layer 46 in the depth direction (Z) of the fluid intake layer 40 and the second material layer 46 can be positioned between the first material layer 44 and the absorbent core 50 in the depth direction (Z) of the fluid intake layer 40. In various embodiments, the fluid intake layer 40 can be formed of two material layers of nonwoven material bonded together. In various embodiments, the fluid intake layer 40 can be formed of more than two material layers of nonwoven material bonded together. In various embodiments, the fluid intake layer 40 can be formed of at least 2, 3, 4 or 5 material layers of nonwoven material.

Any of a variety of nonwoven materials can be capable of being used for the resilient fluid intake layer 40 to accomplish the above-mentioned functions. The nonwoven materials may be synthetic, cellulosic, or a combination of synthetic and cellulosic materials. For example, each material layer of the fluid intake layer 40 can be constructed utilizing an airlaid, spunbond, tissue, meltblown, spunbond-meltblown-spunbond, or TABCW material. As a multi-layer component of the absorbent article 10, at least two of the material layers of nonwoven material forming the fluid intake layer 40 can be different from each other. For example, referring to FIGS. 2 and 3, the nonwoven material forming each of the first material layer 44 and the second material layer 46 can be different from each other. For example, the fluid intake layer 40 can have a first material layer 44 constructed of a TABCW material and a second material layer 46 constructed of an airlaid cellulosic material. In such an example, the two material layers, 44 and 46, can be bonded together to form the fluid intake layer 40. In such an example, the airlaid cellulosic tissue may have a basis weight ranging from about 10 or 100 gsm to about 250 or 300 gsm. The airlaid cellulosic tissue can be formed from hardwood and/or softwood fibers. An airlaid cellulosic tissue can have a fine pore structure and can provide an excellent wicking capacity, especially for menses. In such an example, the TABCW material may have a basis weight ranging from about 10 or 100 gsm to about 150, 200, 250, or 300 gsm.

In various embodiments, it has been found that a fluid intake layer 40 formed of at least two material layers of nonwoven material can provide the absorbent article 10 with a raised portion 60 that can improve the vertical absorption capability for the absorbent article 10. It has been found that a fluid intake layer 40 providing an absorbent article 10 with a raised portion 60 can further improve the vertical absorption capability for the absorbent article 10 in embodiments in which the fluid intake layer 40 comprises a resilient nonwoven material. A resilient nonwoven material is not merely a thicker component of the absorbent article 10. Rather, a resilient nonwoven material can have mechanical properties which enable the resilient material to mold with and maintain contact with the wearer's body during usage of the absorbent article 10 and allow the absorbent article 10 to maintain its shape during usage. The mechanical properties to measure the resiliency of a nonwoven material are Compression Work and Compression Rate. Compression Work measures the amount of energy absorbed in a sample of nonwoven material when the nonwoven material is compressed under the maximum pressure of 50 gf/cm$^2$. The larger the value of Compression Work with a low slope (i.e., compression modulus) indicates that it is easier to compress the nonwoven sample. Compression Rate measures the percentage of the thickness change in the nonwoven material between two pressure levels (i.e., 0.5 gf/cm$^2$ and 50 gf/cm$^2$). Higher values of Compression Rate indicate that the nonwoven material is easier to compress. Each of Compression Work and Compression Rate can be measured using the KES-FB3-AUTO-A Automatic Compression Tester, available from Kato Tech Co., LTD, Kyoto, Japan (STM 4560).

At least one of the material layers of nonwoven material utilized in the fluid intake layer 40 is a resilient nonwoven material. At least one of the material layers of nonwoven material utilized in the fluid intake layer 40 has a thickness from about 2, 3, 4, or 5 mm to about 5.5, 6, 8, 10, 13, or 15 mm, Compression Work from about 3, 4 or 5 to about 8, 9, or 10 gf cm/cm$^2$, and a Compression Rate from about 40, 45, 50, 55, 60, 65, 70 or 75% to about 80, 85, 90, 95, or 100%. The thickness of the material layer is also known as the height of the material layer as this is a measurement made without additional pressure placed on the nonwoven material.

A nonwoven material suitable for use as a material layer, such as, for example, either material layer 44 or material layer 46, of the fluid intake layer 40 which can provide the desired thickness, Compression Work, and Compression Rate values for the absorbent article 10 is a through air bonded carded web which has been manufactured in such a way as to have overlapping layers (also known as "sublayers"). In various embodiments, the fibers of the cross lapped TABCW can be any desired fiber and a suitable fiber can be bicomponent fibers, such as core/sheath polyethylene/polyethylene terephthalate, having a denier of 5 and a fiber length from about 40 mm to about 60 mm. In various embodiments, the through air bonded carded web can be manufactured utilizing a conventional lapping process ("lapped TABCW"). A conventional lapping process is one in which a nonwoven material is manipulated during the manufacturing process to overlap itself and this overlapping is performed in the machine direction. A nonwoven material manufactured in such a manner results in a nonwoven material having a higher strength in the machine direction than in the cross-machine direction. In various embodiments, a lapped TABCW suitable for use in the fluid intake layer 40 can have from 2, 4, 5 or 6 to about 14, 15 or 16 sublayers. In various embodiments, the through air bonded carded web can be manufactured utilizing a cross-lapping process ("cross lapped TABCW"). A cross lapping process is one in which a nonwoven material experiences a change in the direction of material travel from the machine direction to the cross-machine direction during the manipulation of the nonwoven material to overlap itself. A nonwoven material manufactured in such a manner can result in a reduction in the ratio of strength between the machine direction and the cross-machine direction.

Figure 4:
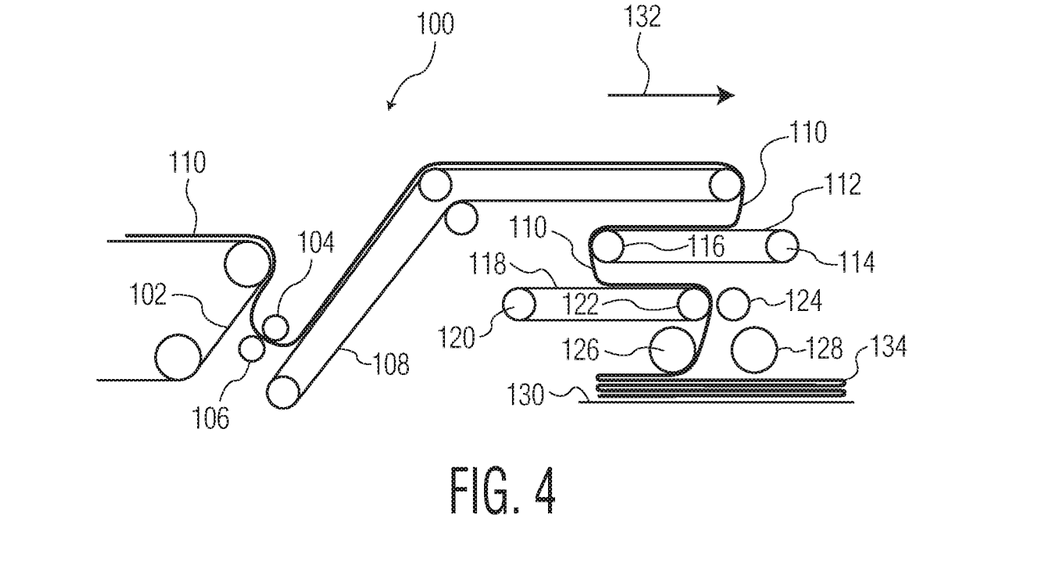
FIG. 4 is a schematic side view of a cross lapper machine for use in a cross lapping process.
Figure 5:
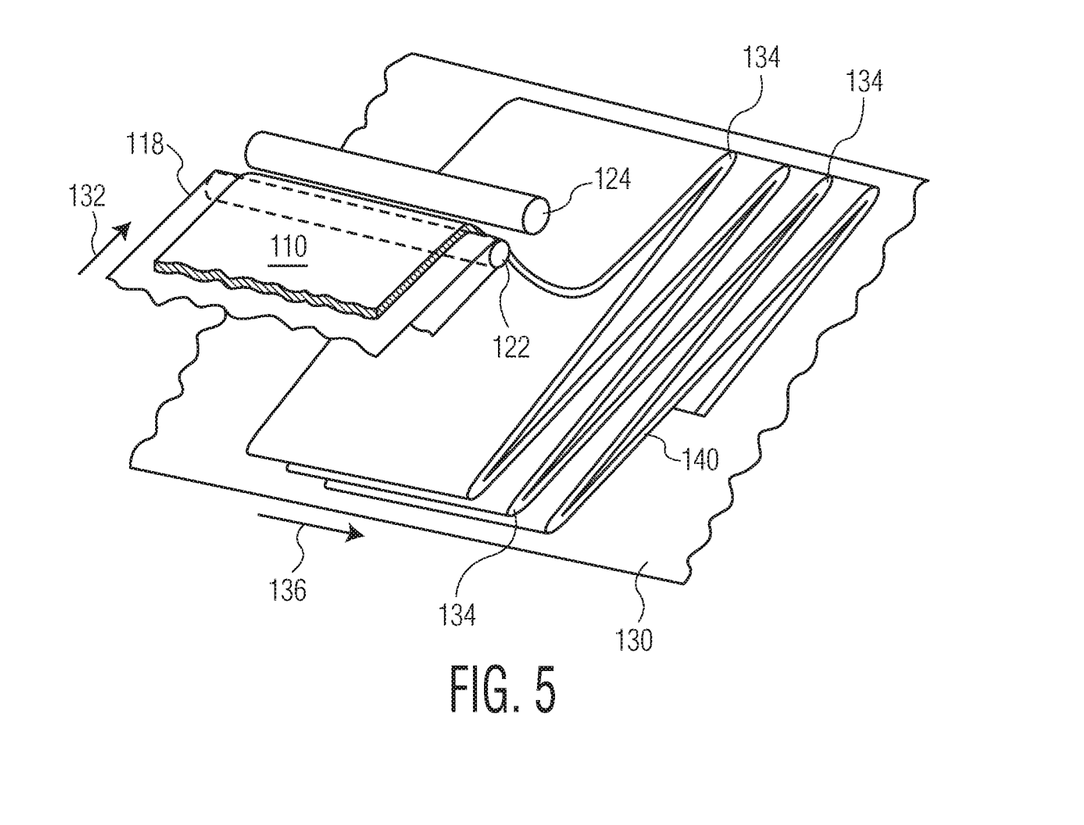
FIG. 5 is a schematic view of a nonwoven material being cross lapped in folds of equal length.

An example of a cross lapping process is illustrated in FIGS. 4 and 5. The cross lapping machine 100 illustrated in FIGS. 4 and 5 is exemplary and other cross lapping processes and machines can be utilized as known to one of ordinary skill in the art. In FIG. 4, a nonwoven material 110 is conveyed on a belt 102, passes between rolls 104 and 106 for consolidating the nonwoven material, and is passed onto a feeder belt 108 of the cross lapper machine 100. The nonwoven material 110 is fed onto a horizontal supporting belt 112 moving around rolls 114 and 116 mounted on an upper carriage (not shown). The nonwoven material 110 passes onto a horizontal laydown belt 118 moving around rolls 120 and 122 mounted on a lower carriage (not shown). The nonwoven material 110 then passes between roll 122 and guide roll 124 and is deposited on a floor conveyor apron 130. The carriages move back and forth in the machine direction 132 across the floor conveyor apron 130 to cause the nonwoven material 110 to overlap itself resulting in folds 134 and sublayers 140 in the nonwoven material 110. The supporting belt 112 is used above the laydown belt 118 to provide a constant path length from the feeder belt 108 to the floor conveyor apron 130. Rolls 126 and 128 can press the folds 134 and sublayers 140 into place on the floor conveyor apron 130. The floor conveyor apron 130 is also moving and conveys the nonwoven material 110 laterally (i.e., in the cross-machine direction 136) to the direction of nonwoven material laydown to form partially overlapping sublayers 140. FIG. 5 illustrates cross lapping the nonwoven material 110 in sublayers 140 of substantially similar length. For simplicity, only rolls 122 and 124 of the cross lapper machine 100 and a portion of the laydown belt 118 are shown. The nonwoven material 110 can be formed with overlapping sublayers 140 wherein a sublayer 140 is formed by moving roll 122 across floor conveyor apron 130 in a first direction and reversing the direction of movement for a distance. When the direction of the roll 122 is reversed a fold 134 is created in the nonwoven material 110. When the desired distance of the sublayer 140 has been formed, the direction of the roll 122 is reversed again. The process is repeated to continue to overlap the nonwoven material 110. Meanwhile, the floor conveyor apron 130 conveys the sublayers 140 of the nonwoven material 110 away from the cross lapper machine 100 (i.e., in the cross-machine direction 136 when compared with the cross-lapper machine 100) so that the sublayers 140 partially overlap each other. In various embodiments, the cross lapped TABCW suitable for use in the fluid intake layer 40 can have from 4, 5 or 6 sublayers 140 to about 14, 15 or 16 sublayers 140.

A TABCW nonwoven material can be carded in such a manner that more fibers are oriented in a given direction, e.g., the machine direction, than fibers oriented in another direction, e.g., the cross machine direction. Overlapping the TABCW material onto itself (a lapped TABCW) can result in sublayers 140 with the majority of the fibers oriented in the same given direction, e.g., the machine direction. A cross lapped TABCW nonwoven material can have sublayers 140 which partially overlap each other due to the change in the direction of the nonwoven material during formation of the cross lapped TABCW. The partial overlap of the sublayers 140 of the nonwoven material 110 can result in fibers of each individual sublayer 140 having a fiber orientation which can be different than the fiber orientation of the fibers of a different individual sublayer 140 of the cross lapped TABCW. Due to the change in the direction of the nonwoven material during the cross lapping process, each sublayer 140 will be positioned at an angle to each other sublayer 140 in the cross lapped TABCW resulting in the orientation of the fibers in each sublayer 140 being different from another sublayer 140. A cross lapped TABCW can have multiple sublayers 140 in which a first sublayer 140 of the cross lapped TABCW can have a first fiber orientation and a second sublayer 140 of the cross lapped TABCW can have a second fiber orientation and the degree of difference between the first fiber orientation and the second fiber orientation can range from about 15, 20, 25 or 30 degrees to about 90, 100, 110, or 120 degrees.

In various embodiments, the fluid intake layer 40 can have two material layers, 44 and 46, and one of the material layers is a lapped TABCW and the other of the materials is an airlaid material. In various embodiments, the first material layer 44 of the fluid intake layer 40 is a lapped TABCW and the second material layer 46 of the fluid intake layer 40 is an airlaid material. In various embodiments, the first material layer 44 of the fluid intake layer 40 is an airlaid material and the second material layer 46 of the fluid intake layer 40 is a lapped TABCW. The lapped TABCW can be bonded to the airlaid cellulosic material layer in any manner deemed suitable by one of ordinary skill. For example, the airlaid cellulosic material layer may be positioned on a floor conveyor apron prior to the laydown of the lapped TABCW.

In various embodiments, the fluid intake layer 40 can have two material layers, 44 and 46, and one of the material layers is a cross lapped TABCW and the other of the material layers is an airlaid material. In various embodiments, the first material layer 44 of the fluid intake layer 40 is a cross lapped TABCW and the second material layer 46 of the fluid intake layer 40 is an airlaid material. In various embodiments, the first material layer 44 of the fluid intake layer 40 is an airlaid material and the second material layer 46 of the fluid intake layer 40 is a cross lapped TABCW. The cross lapped TABCW can be bonded to the airlaid cellulosic material layer in any manner deemed suitable by one of ordinary skill. For example, the airlaid cellulosic material layer may be positioned on the floor conveyor apron 130 prior to the laydown of the cross lapped TABCW.

The fluid intake layer 40 can be located at various positions along the longitudinal and transverse directions of the absorbent article 10 depending upon the primary location of body exudate intake or the purpose for which the absorbent article 10 is being used. For example, in various embodiments, the fluid intake layer 40 can be positioned so that they are in substantial alignment with the longitudinal centerline 70 and the transverse centerline 72 of the absorbent article 10. It should be understood that the longitudinal centerline 70 is disposed at a location that is equidistant from the longitudinal direction side edges 16 and runs the length of the absorbent article 10 in the longitudinal direction (L), while the transverse centerline 72 is disposed at a location that is equidistant from the first transverse direction end edge 12 and the second transverse direction end edge 14 and runs along the width of the absorbent article 10 in the transverse direction (T). This allows the fluid intake layer 40 to be centrally disposed so that they can be positioned below the main point of body exudate discharge and so that they can act as the primary body exudate receiving area for the absorbent article 10.

However, centralized positioning of the fluid intake layer 40 is not required, and in various embodiments, depending on the primary location where body exudate intake might occur, the fluid intake layer 40 may be substantially aligned with the longitudinal centerline 70 only. Thus, in various embodiments, the fluid intake layer 40 may be shifted in the longitudinal direction (L) towards either transverse direction end edge, 12 or 14, of the absorbent article 10, so that the fluid intake layer 40 is not in substantial alignment with the transverse centerline 72.

In various embodiments, the fluid intake layer 40 can be fully positioned within the central portion 78 of the absorbent article 10. In various embodiments, the fluid intake layer 40 can have a portion positioned within the front portion 74 of the absorbent article 10 and a portion positioned within the central portion 78 of the absorbent article 10. In various embodiments, the fluid intake layer 40 can have a portion positioned with the rear portion 76 of the absorbent article 10 and a portion positioned within the central portion 78 of the absorbent article 10. In various embodiments, the fluid intake layer 40 can have a portion positioned in each of the front portion 74, central portion 78, and rear portion 76 of the absorbent article 10. In various embodiments, the fluid intake layer 40 can be fully positioned within the rear portion 76 of the absorbent article 10 such as may be desired in an absorbent article 10 for overnight usage.

As the fluid intake layer 40 defines the raised portion 60 of the absorbent article 10, the raised portion 60 is positioned in the same location of the absorbent article 10 as the fluid intake layer 40.

The raised portion 60 can provide the absorbent article 10 with at least two different portions of the absorbent article 10 having different heights. A first portion of the absorbent article 10 wherein the raised portion 60 is positioned can define a first height 90 in the depth direction (Z) of the absorbent article 10 and a second portion of the absorbent article 10 wherein the raised portion 60 is not located can define a second height 92 in the depth direction (Z) of the absorbent article 10. The first height 90 can be measured from the topsheet 20, through the absorbent article 10 in the first portion of the absorbent article 10 wherein the raised portion 60 is positioned, and to the backsheet 22. The second height 92 can be measured from the topsheet 20, through the absorbent article 10 in a second portion of the absorbent article 10 which does not define the raised portion 60, and to the backsheet 22. FIG. 2 provides an exemplary illustration of a location of the first height 90 and a location of the second height 92. In the example illustrated in FIG. 2, the first height 90 is located in the region of the fluid intake layer 40 and the raised portion 60 which is positioned in the central portion 78 of the absorbent article 10. In the example illustrated in FIG. 2, the second height 92 is illustrated as being closer to a longitudinal edge 16 in a transverse direction (T) from the fluid intake layer 40 while still being measured in the central portion 78 of the absorbent article 10. It is to be understood that the second height 92 can be measured in any portion of the absorbent article 10 which does not contain the fluid intake layer 40 which defines the raised portion 60 of the absorbent article 10. The first height 90 of the absorbent article 10 as measured in the depth direction (Z) of the absorbent article 10 can be from about 3.5, 4, 4.5, or 5 mm to about 5.5, 6, 6.5, 7, 7.5, 8, 8.5, 9, 9.5, or 10 mm. The second height 92 of the absorbent article 10 as measured in the depth direction (Z) of the absorbent article 10 can be from about 1.5, 2, 2.5 or 3 mm to about 3.5, 4, 4.5, or 5 mm. The first height 90 of the absorbent article 10 can be from about 100, 125, 150, or 175% to about 200, 225, 250, 265, 275, or 300% greater than the second height 92 of the absorbent article 10. It is contemplated that the first height 90 can be outside of these described ranges and still be within the scope of the present disclosure.

As the fluid intake layer 40 is formed of a material as described herein, the fluid intake layer 40 can provide the absorbent article 10 with mechanical properties which can define the resiliency of the absorbent article 10. As described herein, a material layer which forms the fluid intake layer 40 can have mechanical properties such as Compression Work and Compression Rate. Use of such a material layer in the fluid intake layer 40 of an absorbent article 10 can provide the absorbent article 10 with a Compression Work and a Compression Rate. Each of Compression Work and Compression Rate can be measured using the KES-FB3-AUTO-A Automatic Compression Tester, available from Kato Tech Co., LTD, Kyoto, Japan (STM 4560). The absorbent article 10 can have a Compression Work from about 1, 2, or 3 gf cm/cm$^2$ to about 4 or 5 gf cm/cm$^2$ and a Compression Rate from about 30, 40, 55 or 60% to about 70 or 75%.

In various embodiments, the fluid intake layer 40 can be at least partially hydrophilic. In various embodiments, the hydrophilicity of the fluid intake layer 40 can be increased or created via treatment of the fluid intake layer 40 with surfactants.

In various embodiments, to further enhance the ability of the absorbent article 10 to transfer body exudates in the depth (Z) direction from the topsheet layer 20 toward any lower layers in the absorbent article 10 as well as to enhance the ability of the fluid intake layer 40 to conform to the wearer's body based on its ability to bend, the fluid intake layer 40 can have an opening 54 in the fluid intake layer 40 which can be any suitable shape, such as ovular, circular, rectangular, square, triangular, etc. In various embodiments, the opening 54 in the fluid intake layer 32 can be elongate and can be oriented in the longitudinal direction of the absorbent article 10. To form the opening 54 in the fluid intake layer 40, each of the first material layer 44 and the second material layer 46 of the fluid intake layer 40 can have an opening, 62 and 66, respectively. The opening 62 of the first material layer 44 can be bounded by a perimeter 64 which can form an inner border or inner edge of the first material layer 44 of the fluid intake layer 40. The opening 66 of the second material layer 46 can be bounded by a perimeter 68 which can form an inner border or inner edge of the second material layer 46 of the fluid intake layer 40. The opening 54 of the fluid intake layer 40 can leave a portion of the absorbent core 50 exposed and visible due to the lack of presence of the material, i.e., a void space, of the fluid intake layer 40 at the opening 54.

The opening 54 can be located at various positions along the longitudinal and transverse directions of the fluid intake layer 40 depending upon the primary location of body exudate intake or the purpose for which the absorbent article 10 is being used. For example, in various embodiments, the fluid intake layer 40 and the opening 54 in the fluid intake layer 40 can be positioned so that it is in substantial alignment with the longitudinal centerline 76 and the transverse centerline 78 of the absorbent article 10. This allows the opening 54 to be centrally disposed so that it can be positioned below the main point of body exudate discharge and so that it can act as the primary body exudate receiving area for the absorbent article 10.

However, centralized positioning of the fluid intake layer 40 and the opening 54 of the fluid intake layer 40 is not required, and in various embodiments, depending on the primary location where body exudate intake might occur, the fluid intake layer 40 and the opening 54 of the fluid intake layer 40 may be substantially aligned with the longitudinal centerline 76 only. Thus, in various embodiments, the fluid intake layer 40 and the opening 54 of the fluid intake layer 40 may be shifted in the longitudinal direction towards either transverse direction end edge, 12 or 14, of the absorbent article 10, so that the opening 54 of the fluid intake layer 40 is not in substantial alignment with the transverse centerline.

The opening 54 in the fluid intake layer 40 can have a longitudinal length from about 15, 20, 30 or 50 mm to about 60, 75, 100 or 150 mm and can have a transverse width from about 10, 15, 20 or 30 mm to about 40, 60 or 80 mm. The opening 54 in the fluid intake layer 40 can have a length that is from about 15, 20 or 25% to about 70, 75, or 80% of the overall longitudinal length of the fluid intake layer 40 in the longitudinal direction (L). The opening 54 in the fluid intake layer 40 can have a width that can be from about 20, 25 or 30% to about 70, 75 or 80% of the overall width of the fluid intake layer 40 in the transverse direction (T). The opening 54 in the fluid intake layer 40 can serve to funnel and direct body exudates from the topsheet layer 20 and towards lower layers of the absorbent article 10 in the depth (Z) direction. The opening 54 in the fluid intake layer 40 can also form a cup or well-like structure for holding body exudates and preventing its leakage away from a central region of the absorbent article 10 and towards the edges of the absorbent article 10.

In various embodiments, the absorbent article 10 can have at least two fluid intake layers 40. In such embodiments, a first fluid intake layer 40 can be positioned in the central portion 78 of the absorbent article 10 and a second fluid intake layer 40 can be positioned in the rear portion 76 of the absorbent article. In various embodiments, both fluid intake layers 40 are formed without an opening 54 such as described herein. In various embodiments, both fluid intake layers 40 are formed with an opening 54 such as described herein. In various embodiments, the fluid intake layer 40 in the central portion 78 is formed without an opening 54 such as described herein and the fluid intake layer 40 in the rear portion 76 is formed with an opening 54 such as described herein. In various embodiments, the fluid intake layer 40 in the central portion 78 is formed with an opening 54 such as described herein and the fluid intake layer 40 in the rear portion 76 is formed without an opening 54 such as described herein.

Absorbent Core:

An absorbent core 50 can be positioned between the topsheet layer 20 and the backsheet layer 22. The absorbent core 50 can be positioned beneath the fluid intake layer 40 in the depth direction (Z) of the absorbent article 10. The absorbent core 50 can generally be any single layer structure or combination of layer components, which can demonstrate some level of compressibility, conformability, be non-irritating to a wearer's skin, and capable of absorbing and retaining liquids and other body exudates. Additionally, the absorbent core 50 can provide additional capacity to absorb and retain body exudates such as menses. In various embodiments, the absorbent core 50 can be formed from a variety of different materials and can contain any number of desired layers. For example, the absorbent core 50 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of a wood pulp fluff can be identified with the trade designation NB 416, available from Weyerhaeuser Corp., and is a bleached, highly absorbent wood pulp containing primarily soft wood fibers.

In various embodiments, if desired, the absorbent core 50 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and α-olefins, poly(vinyl pyrrolidone), poly(vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 50 in any amount as desired.

Regardless of the combination of absorbent materials used in the absorbent core 50, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

The shape of the absorbent core 50 can vary as desired and can comprise any one of various shapes including, but not limited to, triangular, rectangular, dog-bone and elliptical shapes. In various embodiments, the absorbent core 50 can have a shape that generally corresponds with the overall shape of the absorbent article 10. The dimensions of the absorbent core 50 can be substantially similar to those of the absorbent article 10, however, it will be appreciated that the dimensions of the absorbent core 50 while similar, will often be less than those of the overall absorbent article 10, in order to be adequately contained therein.

By way of example, suitable materials and/or structures for the absorbent core 50 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al., each of which is hereby incorporated by reference thereto in its entirety.

As described above, in various embodiments, an absorbent core 50 can be a single layer structure and can include, for example, a matrix of cellulosic fluff and superabsorbent material. In various embodiments, an absorbent core 50 can have at least two layers of material, such as, for example, a body facing layer and a garment facing layer. In various embodiments, the two layers can be identical to each other. In various embodiments, the two layers can be different from each other. In such embodiments, the two layers can provide the absorbent article 10 with different absorption properties as deemed suitable. In various embodiments, the body facing layer of the absorbent core 50 may be constructed of an airlaid material and the garment facing layer of the absorbent core 50 may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

Backsheet Layer:

The backsheet layer 22 is generally liquid impermeable and is the portion of the absorbent article 10 which faces the garment of the wearer. The backsheet layer 22 can permit the passage of air or vapor out of the absorbent article 10 while still blocking the passage of liquids. Any liquid impermeable material may generally be utilized to form the backsheet layer 22. The backsheet layer 22 can be composed of a single layer or multiple layers, and these one or more layers can themselves comprise similar or different materials. Suitable material that may be utilized can be a microporous polymeric film, such as a polyolefin film of polyethylene or polypropylene, nonwovens and nonwoven laminates, and film/nonwoven laminates. The particular structure and composition of the backsheet layer 22 can be selected from various known films and/or fabrics with the particular material being selected as appropriate to provide the desired level of liquid barrier, strength, abrasion resistance, tactile properties, aesthetics and so forth. In various embodiments, a polyethylene film can be utilized that can have a thickness in the range of from about 0.2 or 0.5 mils to about 3.0 or 5.0 mils. An example of a backsheet layer 22 can be a polyethylene film such as that obtainable from Pliant Corporation, Schaumburg, Ill., USA. Another example can include calcium carbonate-filled polypropylene film. In still another embodiment, the backsheet layer 22 can be a hydrophobic nonwoven material with water barrier properties such as a nonwoven laminate, an example of which can be a spunbond, meltblown, meltblown, spunbond, four-layered laminate. The backsheet layer 22 can, therefore, be of a single or multiple layer construction, such as of multiple film layers or laminates of film and nonwoven fibrous layers. Suitable backsheet layers 22 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

Additional Layers:

In various embodiments, an absorbent article 10 can optionally include additional layers within the absorbent system 30 of the absorbent article 10. Such additional layers can include a surge layer and/or a distribution layer.

Figure 7:
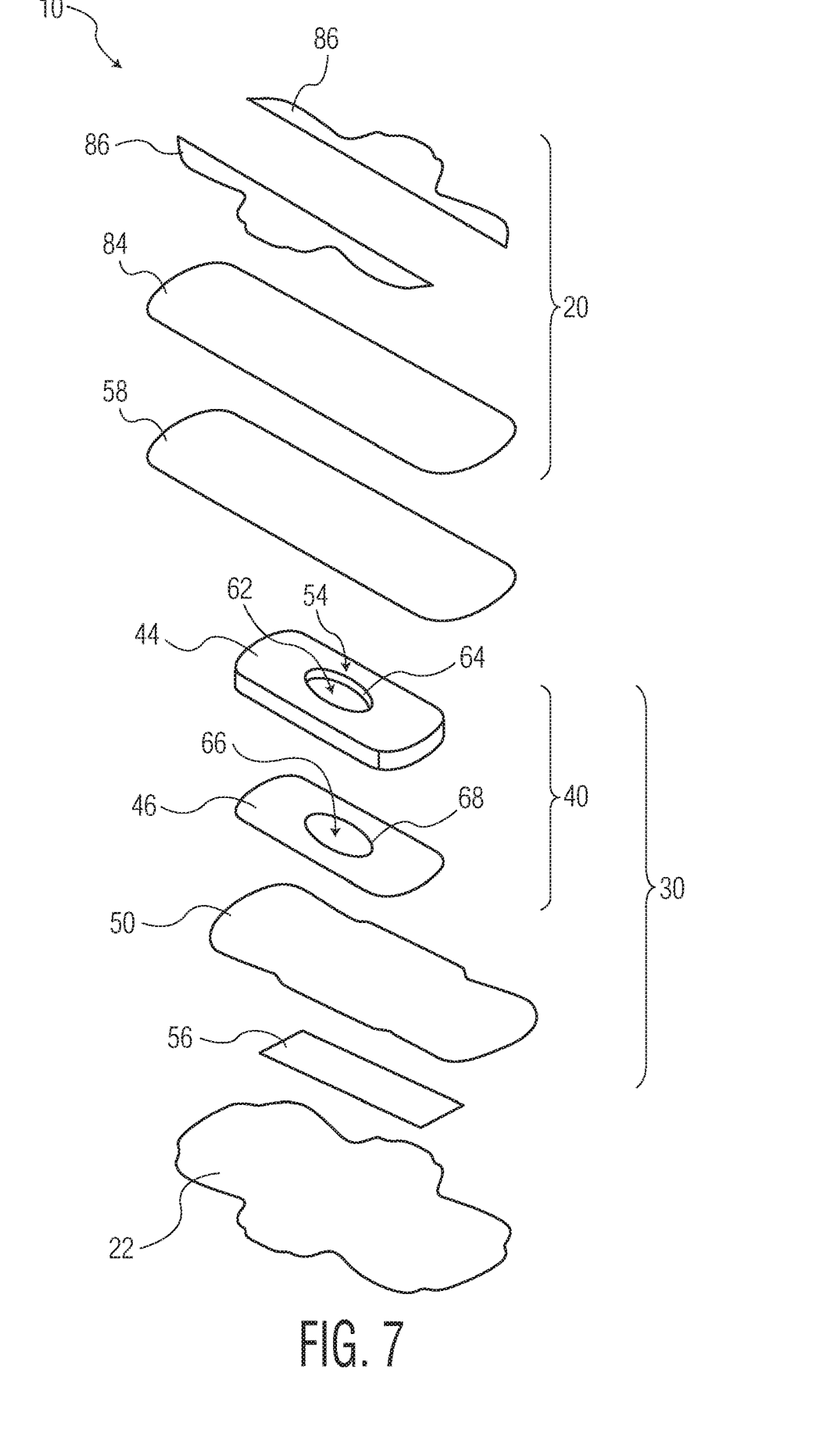
FIG. 7 is an exploded perspective view of an embodiment of an absorbent article.

Surge Layer:

A surge layer can be positioned between the topsheet layer 20 and the fluid intake layer 40 in the depth direction (Z) of the absorbent article 10. An example of a surge layer 58 is illustrated in FIG. 7. A surge layers 58 can be constructed of any woven or nonwoven material that is easily penetrated by body exudates. The surge layer 58 can help to absorb, decelerate, and diffuse surges or gushes of liquid that may be rapidly introduced into the absorbent article 10. The surge layer 58 can rapidly accept and temporarily hold the liquid prior to releasing the liquid into, for instance, the fluid intake layer 40 and/or the absorbent core 50 or any other layer of the absorbent article 10. Various woven fabrics and nonwoven webs can be used to construct the surge layers. For example, the surge layer 58 can comprise a nonwoven fabric layer composed of a meltblown or spunbond web of polyolefin or polyester filaments. Such nonwoven fabric layers may include conjugate, biconstituent and homopolymer fibers of staple or other lengths and mixtures of such fibers with other types of fibers. The surge layer 58 can also be a bonded card web or an airlaid web composed of natural and/or synthetic fibers. The bonded carded web may, for example, be a powder bonded carded web, an infrared bonded carded web, or a through air bonded carded web. The bonded carded webs can optionally include a mixture or blend of different fibers. The surge layer 58 typically has a basis weight of less than about 100 gsm, and in some embodiments, from about 10 gsm to about 40 gsm.

Distribution Layer:

In various embodiments, such as the exemplary illustration of FIG. 7, the absorbent system 30 can have a distribution layer 56 positioned below the absorbent core 50. The distribution layer 56 can increase absorbency of the absorbent article 10. The distribution layer 56 can be constructed of various materials such as, but not limited to, hydroentangled webs, through air bonded carded webs, meltblown webs, and meltblown microfiber webs. The distribution layer 56 can include a hydrophilic material. The distribution layer 56 can be smaller in size than the absorbent core 50 of the absorbent article 10.

In various embodiments, the distribution layer 56 can have a longitudinal length from about 80, 90, 100, 110, 120, 125 or 130 mm to about 135, 140, 150, 160, 170, 180 or 190 mm and can have a transverse width from about 30, 35 or 40 mm to about 45, 50, 55 or 60 mm. In various embodiments, the distribution layer 56 can have a density of greater than about 0.1 grams per cubic centimeter. The density can be calculated utilizing the formula: density=basis weight (gsm)/thickness (mm)/1000. In various embodiments, the distribution layer 56 can have a basis weight from about 10, 20, 25, 30 or 50 gsm to about 60, 70, 80, 90, 100, 120, 140, 150, 160, 180 or 200 gsm.

In various embodiments, the distribution layer 56 can be a hydroentangled web. The hydroentangled web can include a hydroentangled spunbond material and a pulp material. The hydroentangled spunbond material can include a polypropylene material. The spunbond material can be present in an amount from about 10% or 15% to about 20% or 25% of the hydroentangled web. The pulp material can be present in an amount from about 75% or 80% to about 85% or 90% of the hydroentangled web. The hydroentangled web can have a basis weight from about 30 or 60 gsm to about 90 or 200 gsm. Without being bound by theory, it is believed that a higher basis weight hydroentangled web can improve the absorbency of the distribution layer 56. It is further believed that an improved absorbency of the distribution layer 56 can further result in an improved fluid retention capacity of the absorbent article 10. The basis weight of the hydroentangled web can be balanced with the desired flexibility of the absorbent article 10. In various embodiments, the distribution layer 56 can include a bicomponent fluid distribution layer, which can increase absorbency by providing a high void space and may be made of a through air bonded carded web, having a basis weight, in an embodiment, of between about 25 gsm and 100 gsm. In various embodiments, the distribution layer 56 can be a meltblown microfiber web of polypropylene material and can have a basis weight from about 10 or 20 gsm to about 30, 50 or 100 gsm. In various embodiments, the meltblown microfiber web can be treated with wetting agents for adequate handling of body exudates. Examples of wetting agents can include, but are not limited to, surface active agents (or surfactants) having a hydrophilic lipophilic balance (HLB) of at least 6, 7 or 18. A variety of surfactants can be used and can include, but are not limited to, anionic, cationic, or neutral from a charge standpoint. Mixtures of surfactants and other wetting agents can also be used. A wetting agent add-on can range from about 0.1 or 0.2% to about 5 or 10%. In various embodiments, an add-on amount can be higher than 10%. For example, the meltblown microfiber web can be treated to impart hydrophlicity by either Aerosol GPG of Cytec or Ahcovel Base N-62 for example. Such material is available from Yuhan-Kimberly Ltd., Seoul, Korea and FlberTex, Malaysia.

Embossing:

In various embodiments, the absorbent article 10 can have one or more embossed regions formed in one or more layers of the absorbent article 10. Generally, the embossed regions can be described as channels formed in the absorbent article 10 due to deformations of the layer(s) of the absorbent article 10. The embossed regions are formed in any suitable pattern to not only create an aesthetically pleasing surface, but also to facilitate funneling of body exudates towards a desired location in the absorbent article 10, such as, for example, the fluid intake layer 40 of the absorbent article 10. The embossed regions may also improve the consistency of the fit properties of the absorbent article 10, both before and after receiving body exudates. The embossed regions may be provided in either a symmetric or asymmetric manner to the absorbent article 10.

Further, the embossed regions may be formed using any known conventional technique known in the art. Suitable techniques include, for example, the use of raised elements to impart the desired embossing pattern to create compressed channels in the layer(s) of the absorbent article 10. For instance, a suitable process may include using thermal bonding wherein the absorbent article 10 is passed through two rolls (e.g., steel, rubber, etc) where one is engraved with an embossing pattern and the other is flat. One or both rolls may be heated. In addition, thermal and/or ultrasonic bonding techniques may be employed to create the embossing regions.

The absorbent article 10 can have at least one embossed region 32. The embossed region 32 can provide both an aesthetically pleasing appearance and topography to the absorbent article 10 which can direct body exudates to a desired location, such as, for example, the fluid intake layer 40, and prevent leakage and/or pooling of the body exudate around the edge of the absorbent article 10.

In various embodiments, the embossed region 32 can generally extend around the entire absorbent article 10 in a generally oblong shape. In various embodiments, the embossed region 32 can have a protrusion(s) in the longitudinal and/or transverse directions of the absorbent article 10 to provide any additional desired shaping to the embossed region 32. The embossed region 32 can generally surround and frame the fluid intake layer 40 of the absorbent article 10. In various embodiments, the embossed region 32 surrounds the fluid intake layer 40 without penetrating into the fluid intake layer 40. In various embodiments, a distance separating the fluid intake layer 40 from an embossed region 32 can be from about 1, 1.5, 2, 2.5, or 3 mm to about 3.5, 4, 4.5, 5, or 5.5 mm. FIG. 1 provide an exemplary illustration of an embossed region 32 in which the embossed region 32 has an opposing pair of longitudinally extending side portions 32a which are present in the central portion 78 of the absorbent article 10 and each extend into the front portion 74 and the rear portion 76 of the absorbent article 10. The embossed region 32 also has an opposing pair of transversely extending end portions 32b which are present in each of the front portion 74 and the rear portion 76 of the absorbent article 10 and which connect the longitudinally extending side portions 32a. While the embossed region 32 is illustrated as extending the majority of the absorbent article length 80 it is to be understood that the embossed region 32 can be any size and shape as desired and can be located in only the central portion 78 of the absorbent article 10 or can extend into either or both of the front portion 74 and/or rear portion 76 of the absorbent article 10.

In various embodiments, the absorbent article 10 can have one or more second embossed regions 34. A second embossed region 34 can be positioned in the front portion 74 and/or rear portion 76 of the absorbent article 10. In various embodiments in which an embossed region 32 extends generally the majority of the absorbent article length 80, the one or more second embossed regions 34 can be positioned in closer proximity to the fluid intake layer 40 in the front portion 74 and/or rear portion 76 of the absorbent article 10. In the exemplary illustration of FIG. 1, the second embossed regions 34 can have a semi-circular shape, although any other suitable shape can be used. The second embossed regions 34 can be formed through any of the layers of the absorbent article 10 without penetrating into the fluid intake layer 40. In various embodiments in which the absorbent article 10 has an embossed region 32 and at least one second embossed region 34, the combination of the embossed region 32 and the second embossed region 34 can surround and frame the fluid intake layer 40 of the absorbent article 10.

Wings:

The wings 26 can be constructed from materials described above with respect to the topsheet layer 20 and the backsheet layer 22. In various embodiments, the wings 26 can comprise an extension of a layer of material within the topsheet layer 20, the backsheet layer 22, and/or the absorbent system 30. By way of example, the wings 26 can be formed by an extension of the topsheet layer 20 and backsheet layer 22 that are then bonded together along peripheral seal 24. Such wings 26 can be integrally formed with the main portion of the absorbent article 10. Alternatively, the wings 26 can be formed independently and separately attached to an intermediate section of the absorbent article 10. Wings 26 that are made independent of the other components of the absorbent article 10 can be bonded to a portion of the topsheet layer 20 and/or backsheet layer 22. Examples of processes for manufacturing absorbent articles 10 and wings 26 include, but are not limited to, those described in U.S. Pat. No. 4,059,114 to Richards, U.S. Pat. No. 4,862,574 to Hassim, et al., U.S. Pat. No. 5,342,647 to Heindel, et al., U.S. Pat. No. 7,070,672 to Alcantara, et al., U.S. Publication No., 2004/0040650 to Venturino, et al., and international publication WO1997/040804 to Emenaker, et al., each of which are hereby incorporated by reference thereto in its entirety.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. An absorbent article comprising:
   a. a longitudinal direction, a transverse direction, and a depth direction;
   b. a topsheet layer and a backsheet layer; and
   c. an absorbent system positioned between the topsheet layer and the backsheet layer, the absorbent system comprising:
      i. a fluid intake layer comprising a first material layer that is a cross lapped through air bonded carded web having from 2 to 16 sublayers wherein a first of the sublayers has a first fiber orientation and a second of the sublayers has a second fiber orientation wherein the first fiber orientation and the second fiber orientation are different from about 15 to about 120 degrees and a second material layer bonded to the first material layer; and
      ii. an absorbent core.

2. The absorbent article of claim 1 wherein the second material layer of the fluid intake layer is an airlaid material.

3. The absorbent article of claim 1 wherein the fluid intake layer has a thickness from about 2 mm to about 15 mm.

4. The absorbent article of claim 1 wherein the fluid intake layer has a Compression Work from about 3 gf cm/cm$^2$ to about 10 gf cm/cm$^2$.

5. The absorbent article of claim 1 wherein the fluid intake layer has a Compression Rate from about 40% to about 100%.

6. The absorbent article of claim 1 wherein the fluid intake layer defines a raised portion.

7. The absorbent article of claim 6 wherein the absorbent article has a first height at the location of the raised portion from about 3.5 mm to about 10 mm.

8. The absorbent article of claim 1 having a Compression Work from about 4 to about 8 gf cm/cm$^2$.

9. The absorbent article of claim 1 having a Compression Rate from about 30 to about 75%.

10. The absorbent article of claim 1 wherein the fluid intake layer further comprises an opening.

11. The absorbent article of claim 1 wherein the absorbent article further comprises an embossed region.

12. The absorbent article of claim 11 wherein the embossed region does not penetrate into the fluid intake layer.

13. The absorbent article of claim 12 wherein the embossed region is separated from the fluid intake layer a distance from about 1 mm to about 5.5 mm.

14. The absorbent article of claim 11 wherein the absorbent article further comprises a second embossed region.

15. The absorbent article of claim 1 wherein the fluid intake layer has a body facing surface area and the absorbent article has a total body facing surface area wherein the body facing surface area of the fluid intake layer is from about 5% to about 20% of the total body facing surface area of the absorbent article.

* * * * *